United States Patent [19]

Tessler

[11] 4,297,299
[45] Oct. 27, 1981

[54] NOVEL N-(ALKYL)-N-(2-HALOETHYL)-AMINOMETHYLPHOSPHONIC ACIDS, A METHOD FOR THE PREPARATION THEREOF AND THEIR USE IN THE PREPARATION OF STARCH ETHER DERIVATIVES

[75] Inventor: Martin M. Tessler, Edison, N.J.

[73] Assignee: National Starch and Chemical Corporation, Bridgewater, N.J.

[21] Appl. No.: 182,547

[22] Filed: Aug. 29, 1980

Related U.S. Application Data

[60] Division of Ser. No. 110,926, Jan. 10, 1980, Pat. No. 4,260,738, which is a continuation-in-part of Ser. No. 66,526, Aug. 15, 1979, Pat. No. 4,243,479.

[51] Int. Cl.$^3$ .............................................. C07F 9/38
[52] U.S. Cl. .................................. 260/502.5; 536/49; 162/175
[58] Field of Search ...................................... 260/502.5

[56] References Cited

U.S. PATENT DOCUMENTS

| | | | |
|---|---|---|---|
| 3,288,846 | 11/1966 | Irani et al. | 260/502.5 |
| 3,298,956 | 1/1967 | Irani et al. | 260/502.5 |
| 3,459,793 | 8/1969 | Shen et al. | 260/502.5 |
| 3,969,341 | 7/1976 | Tessler | 260/502.5 |
| 4,160,779 | 7/1979 | Maier | 260/502.5 |

FOREIGN PATENT DOCUMENTS

1142294  2/1969  United Kingdom ............. 260/502.5

OTHER PUBLICATIONS

Moedritzer et al., "J. Org. Chem.", vol. 31, (1966), pp. 1603–1607.
Fields, "J. Am. Chem. Soc.", vol. 74, (1952), pp. 1528–1531.

*Primary Examiner*—Joseph E. Evans
*Attorney, Agent, or Firm*—Edwin M. Szala; Margaret B. Kelley

[57] ABSTRACT

Starch ether derivatives are prepared by reacting a starch base with N-(2-haloethyl)iminobis(methylene)diphosphonic acid or with a N-(alkyl)-N-(2-haloethyl)aminomethylphosphonic acid. The derivatives contain aminophosphonic acid groups (or their salts) as zwitterion substituents which consist of either one or two anionic methylene phosphonic acid groups bound to a cationic nitrogen. Their cationic or anionic characteristics may be increased by introducing suitable cationic or anionic groups either by simultaneous reaction with the aminophosphonic acid reagent or by consecutive reaction either prior to or subsequent to the aminophosphonic acid reaction. They are especially useful as pigment retention aids in paper making processes. The N-(alkyl)-N-(2-haloethyl)aminomethylphosphonic acids are new reagents prepared by reacting a N-(2-haloethyl)alkylamine hydrohalide (e.g. N-(2-chloroethyl)ethylamine hydrochloride or N-(2-chloroethyl)cyclohexylamine hydrochloride), phosphorous acid, formaldehyde, and aqueous hydrochloric acid at 110° to 125° C. for 1 to 6 hours.

3 Claims, No Drawings

NOVEL N-(ALKYL)-N-(2-HALOETHYL)-AMINOMETHYL-PHOSPHONIC ACIDS, A METHOD FOR THE PREPARATION THEREOF AND THEIR USE IN THE PREPARATION OF STARCH ETHER DERIVATIVES

This application is a division of application Ser. No. 110,926, filed Jan. 10, 1980, now U.S. Pat. No. 4,260,738, which is a continuation-in-part of my co-pending application Ser. No. 66,526, filed Aug. 15, 1979 now U.S. Pat. No. 4,243,479.

BACKGROUND OF THE INVENTION

This invention relates to novel zwitterion starch ether derivatives and to a method for their preparation. This invention also relates to modified zwitterion starch ether derivatives which contain, in addition to the zwitterion substituent groups, other cationic, cationogenic, or anionic substituent groups and to a method for their preparation. This invention also relates to the use of these novel zwitterion and modified zwitterion starch ether derivatives in various papermaking processes, especially to their use as pigment retention aids. This invention is also directed to a novel reagent useful for preparing the zwitterion starch ether derivatives.

As used herein, the term "zwitterion starch ether derivatives" includes amphoteric starch ether derivatives wherein the anionic and cationic or cationogenic substituent groups are both bonded to the same reaction site on the starch molecule through a zwitterion substituent group.

As used herein, the term "amphoteric starch ether derivatives" refers to a starch ether derivative wherein the anionic and cationic or cationogenic substituent groups are bonded to different reaction sites on the starch molecule.

As used herein, the term "cationogenic" refers to nonionic substituents capable of forming cations, e.g. diethylaminoethyl ether substituents.

As used herein, the term "paper" includes sheet-like masses and molded products made from fibrous cellulosic materials which may be derived from natural sources as well as from synthetics such as polyamides, polyesters, and polyacrylic resins, and from mineral fibers such as asbestos and glass. In addition, papers made from combinations of cellulosic and synthetic materials are applicable herein. Paperboard is also included within the broad term "paper".

It is well known to add cationic or anionic substituent groups to starch to form cationic or anionic starch derivatives. A discussion of the preparation of cationic or anionic starch ether derivatives may be found in "Starch: Chemistry and Technology", Vol. II, ed. by R. L. Whistler and E. F. Pascall (New York: Academic Press, 1967), pages 406–414 and 312–326, respectively.

It is also known to add both cationic and anionic substituent groups to starch to form amphoteric starch ether derivatives. Most of the prior art methods used to prepare amphoteric starch ether derivatives involve either an "in situ" formation of the amphoteric starch ether derivatives by simultaneous reaction of two different chemical modifying agents with the starch or a multi-step procedure wherein the chemical modifications of the starch are carried out in sequence. In the resulting starch ether derivatives, the cationic and anionic substituent groups are bonded to different reactive sites on the starch molecule. The "in situ" preparation of amphoteric starch ether derivatives is described in U.S. Pat. Nos. 3,459,632 and 4,119,487 and the multi-step procedure is described in U.S. Pat. No. 3,751,422.

It is also known to add cationic and anionic substituent groups to the same reactive site in the starch molecule, thereby forming zwitterion starch ether derivatives. The preparation of a zwitterion starch ether derivative, wherein the zwitterion substituent groups are aminocarboxylic acid groups, is described in U.S. Pat. No. 4,017,460. The derivatives are prepared by reacting the starch base directly with novel reagents obtained by reacting a secondary amine with a 2,3-dihalopropionic acid or an alkyl ester thereof. The resulting zwitterion group contains an anionic carboxyl group bound directly to a cationic amine group.

In contrast to the aminocarboxylic acid zwitterion starch ethers described in U.S. Pat. No. 4,017,460, the novel zwitterion starch ether derivatives of this invention contain, as the zwitterion substituent group, aminophosphonic acids (or their salts). Each substituent contains either one or two anionic methylenephosphonic acid groups bound to a cationic nitrogen.

In addition, the cationic or anionic characteristics of these zwitterion starch ether derivatives may be increased by the introduction of other cationic, cationogenic, or anionic substituent groups onto different reactive sites of the starch molecule.

It is well known to use starch and starch derivatives as aids in various papermaking processes such as wet end, sizing and coating applications. It is also known to use cationic, anionic and amphoteric starch ether derivatives as pigment retention aids. In the case of paper containing added pigments, these pigment retention aids are added to the pulp or stock during the papermaking process for the specific purpose of retaining a greater proportion of such pigments in the paper (rather than have them drain off in the water that is removed during the formation of the sheet). A particularly desirable pigment retention aid would be one which is versatile and which may be used in both neutral and acidic systems (contains alum). Hence, the search continues for novel starch ether derivatives which will improve pigment retention in paper, while being at the same time relatively facile and inexpensive to prepare.

Accordingly, it is an object of the present invention to provide novel zwitterion starch ether derivatives wherein one or two methylenephosphonic acid groups (or salt groups) are bonded to a cationic nitrogen atom and to provide a novel reagent and a method for preparing them.

It is a further object to provide modified zwitterion starch ether derivatives which contain, in addition to the zwitterion substituent groups, additional cationic, cationogenic or anionic substituent groups on different reactive sites of starch and to provide a method for preparing them.

It is further object to provide novel zwitterion and modified zwitterion starch ether derivatives which will be useful in various papermaking processes, especially as pigment retention aids.

It is a further object to provide a paper with improved pigment retention.

SUMMARY OF THE INVENTION

The above and related objects are achieved by the preparation of novel zwitterion starch ether derivatives of the general structures (i) or (ii) or a combination of (i) and (ii),

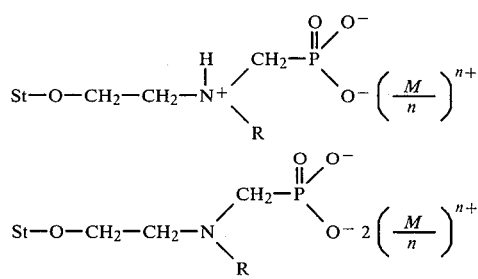

wherein
St—O— represents a starch molecule or a modified starch molecule (wherein the hydrogen of a hydroxyl group of an anhydroglucose unit has been replaced as shown);
R is a $C_1$–$C_6$ straight or branched chain alkyl group, a $C_3$–$C_6$ cycloalkyl group or a

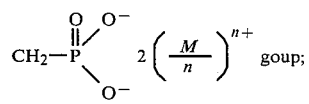 goup;

M is the same or different cation(s); and
n is the valence number of M.

In the method of this invention the starch ether derivatives are prepared by reacting a starch base with about 0.1 to 100% by weight, based on dry starch, of N-(2-haloethyl)iminobis(methylene)diphosphonic acid or with about 0.1 to 100% by weight, based on dry starch, of a N-alkyl-N-(2-haloethyl)aminomethylphosphonic acid and isolating the resulting starch derivatives. The reactions are carried out under alkaline conditions. They may be carried out in an aqueous, aqueous-organic, or substantially dry reaction medium. The reaction is carried out at a pH of 11 to 13 and a temperature of 20° to 100° C. for 0.5 to 20 hours.

The N-(alkyl)-N-(2-haloethyl)aminomethylphosphonic acids, which react with the starch base to form the starch ether derivatives herein, are themselves new reagents which are prepared by reacting a N-(2-haloethyl)alkylamine hydrochloride with formaldehyde and phosphorous acid in aqueous hydrohalic acid at a temperature of 110°–125° C. for 1 to 16 hours.

The starch ether derivatives of this invention may be modified to increase their cationic or anionic characteristics. When increased cationic properties are desired, cationic or cationogenic substituent groups such as diethyl aminoethyl ether groups or 3-(trimethylammonium chloride)-2-hydroxypropyl groups are introduced into the starch molecule using suitable cationic or cationogenic reagents. When increased anionic properties are desired, anionic substituent groups such as 2-sulfo-2-carboxyethyl groups are introduced into the starch molecule using a suitable anionic reagent. Reaction with the cationic, cationogenic, or anionic reagent may be carried out prior to or after the reaction with the aminophosphonic acid (or salt) reagent or the two reactions may be carried out simultaneously.

The novel zwitterion starch ether derivatives and modified zwitterion starch ether derivatives of this invention may be used as wet end additives and in many other applications wherein starch ether derivatives are commonly used. They are particularly useful as pigment retention aids in papermaking processes.

DESCRIPTION OF THE PREFERRED EMBODIMENTS

The applicable starch bases which may be used in preparing the starch ether derivatives herein may be derived from any plant source including corn, potato, sweet potato, wheat, rice, sago, tapioca, waxy maize, sorghum, high amylose corn, or the like. Also included are the conversion products derived from any of the latter bases including, for example, dextrins prepared by the hydrolytic action of acid and/or heat; oxidized starches prepared by treatment with oxidants such as sodium hypochlorite; fluidity or thin-boiling starches prepared by enzyme conversion or mild acid hydrolysis; and derivatized starches such as ethers and esters. The starch base may be a granular starch or a gelatinized starch, i.e., non-granular starch.

The cationic starches (i.e. starches having cationogenic or cationic groups) which may be used to prepare the modified zwitterion starch ether derivatives of this invention are starch derivatives which are prepared, for example, by reacting starch through an etherification or esterification reaction with any reagent which will introduce a cationic or cationogenic group containing nitrogen, sulfur or phosphorous therein. Examples of such groups are the amino (primary, secondary, tertiary, or quaternary), sulfonium and posphonium groups.

The anionic starches (i.e. starches having anionic groups) which may be used to prepare the modified zwitterion starch ether derivatives of this invention are starch derivatives which are prepared, for example, by reacting starch through an etherification or esterification reaction with any reagent which will introduce an anionic group containing oxygen, sulfur or phosphorus therein. Examples of such groups are carboxyalkyl, sulfoalkyl, sulfocarboxyalkyl, and phosphate groups.

The N-(2-haloethyl)iminobis(methylene)disphosphonic acid reagent, which reacts with the starch base to form zwitterion starch ether derivatives containing amino-diphosphonic acid groups (or salt groups), may itself be prepared by reacting a 2-haloethylamine with formaldehyde and phosphorous acid in an aqueous hydrohalic acid. The method is analogous to that disclosed by K. Moedritzer and R. Irani in J. Org. Chem. 31, 1603 (1966). Specifically phosphonium acid, in a stoichiometric amount or in an excess of up to 100%, is dissolved in water and a 2-haloethylamine hydrochloride is added. Aqueous hydrohalic acid is slowly added and the mixture is heated to reflux. Formaldehyde (10–200% excess) is added, and the solution is refluxed for 1–20 hours, preferably 2–6 hours, cooled to room temperature, and stripped of excess water, formaldehyde and hydrohalic acid. The product sometimes crystallizes as a very hard mass. It is preferable to add water and alkali to the acid product to form a 20–50% aqueous solution having a pH of 1.5–2.7. The halo groups for use herein are chloro and bromo. The preferred reagents are 2-chloroethylamine hydrochloride and 2-bromoethylamine hydrobromide. The preferred hydrohalic acid is hydrochloric acid.

The N-(alkyl)-N-(2-haloethyl)aminomethylphosphonic acids, which react with the starch base to form zwitterion starch ether derivatives containing amino-monophosphonic acid groups (or salt groups), are themselves new reagents. They may be prepared by a variation of the procedure described above, except that a N-(2-haloethyl)alkylamine hydrochloride or hydrobromide is used as the starting material. The halo groups for use herein are chloro and bromo. Examples of suitable N-(alkyl)-N-(2-haloethyl)aminomethylphosphonic acids include the N-(methyl)-, N-(ethyl)-, N-(propyl)-, N-(butyl), and N-(cyclohexyl)-N-(2-haloethyl)aminomethylphosphonic acids. The alkyl groups may be linear, branched or cyclic. The preferred reagents for use herein include N-(ethyl)-, N-(n-butyl)- and N-(cyclohexyl)-N-(2-chloroethyl)aminomethylphosphonic acids.

These reagents will be referred to herein as zwitterion reagents and this term is meant to include both the amino-diphosphonic acid reagent, i.e. N-(2-haloethyl)iminobis(methylene)diphosphonic acid, and the new amino-monophosphonic acid reagents, i.e. N-(alkyl)-N-(2-haloethyl)aminomethylphosphonic acids. The practitioner will recognize that these zwitterion reagents are acids or partially neutralized acids under the conditions used for their preparation and storage but are acid salts under the alkaline conditions used for their reactions with the starch base.

The N-(2-haloethyl)alkylamine hydrochlorides, which are used in the preparation of the new amino-monophosphonic acid reagents, are themselves prepared by reacting a 2-(alkylamino)ethanol with thionyl chloride in an organic solvent. Specifically, a 2-(alkylamino)ethanol is added to toluene and the solution is cooled to $-10°$ C. A solution of thionyl chloride in an organic solvent (e.g. toluene) is slowly added while maintaining the temperature at below $-10°$ C. Additional toluene may be added and the temperature is increased to about 75°–100° C. The solution is agitated for 1 hour, cooled and then maintained at 75°–82° C. for 3 hours. After cooling to room temperature, the insoluble product is recovered by filtration. The preferred reagents for use herein include 2-(ethylamino)ethanol, 2-(n-butylamino)ethanol, and 2-(cyclohexylamino)ethanol.

The practitioner will recognize that the reaction conditions used in the above reagent preparations may have to be altered depending on the nature of the starting materials and that it may be possible to prepare the known reagents by other methods.

The starch reactions of this invention are represented by the equations below:

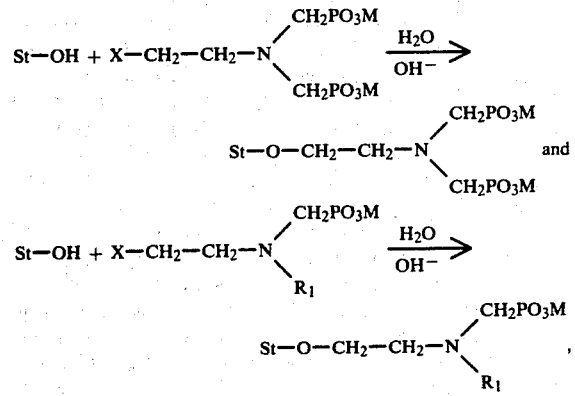

wherein St is a starch base or a modified starch base such as cationic or anionic starches; X is a halogen, preferably chlorine or bromine; $R_1$ is a $C_1$–$C_6$ straight or branched chain alkyl group or a $C_3$–$C_6$ cycloalkyl group; and M is one or more cations depending on the valence of M, preferably selected from the group consisting of hydrogen, ammonium, alkali, and alkaline earth metals. The practitioner will recognize that at the high pH of the starch reactions the nitrogen may not be protonated; however the nitrogen will become protonated when the pH is lowered to 3–7 before isolating the derivative.

The starch ether derivatives prepared by the above reactions are referred to herein as zwitterion starch ether derivatives, and this term is meant to include the starch ether derivatives which contain the amino-diphosphonic acid (or salt) as well as those which contain the amino-monophosphonic acids (or salts). The practitioner will recognize that these zwitterion starch ether derivatives may be either acids, salts, or partial salts depending upon the pH of the solution wherein they are used.

The practitioner will also recognize that the starch molecule is a polymer which contains many anhydroglucose units, each having three free hydroxyl groups (except the non-reducing end glucose units which contain four free hydroxyl groups) which may react with reagent. Thus, the number of such displacements or the degree of substitution (D.S.) will vary with the particular starch, the ratio of reagent to starch, and, to some extent, the reaction conditions. Furthermore, since it is known that the relative reactivity of each of the hydroxyl groups within the anhydroglucose unit is not equivalent, it is probable that some will be more reactive with the reagent than others.

In one method of this invention, the reaction is carried out in an aqueous medium using either an aqueous slurry or an aqueous dispersion of the starch base.

The amount of zwitterion reagent to be employed in the reaction with the starch herein will vary from about 0.1 to 100% by weight, based on the weight of dry starch, depending on such factors as the starch base used, the zwitterion reagent used, the degree of substitution required in the end product, and, to some extent, the reaction conditions used. In general, the preferred amount of reagent to be used when preparing the zwitterion starch ether derivatives containing amino-diphosphonic acid groups or amino-monophosphonic groups (or salt groups) is 0.3 to 10% by weight for granular starches and 15–75% by weight for non-granular starches.

The zwitterion reagent may be added to the reaction mixture as a solid or an aqueous solution. The preferred concentration of the solution is 20–50% by weight, based on weight of reagent. In an alternative method, the zwitterion reagent solution is brought to the desired alkaline pH prior to its addition to the starch base, this being accomplished by the addition of sufficient alkali. In this alternative method, the zwitterion reagent is in the form of a salt rather than an acid or partially neutralized acid when it is introduced to the reaction mixture. In another variation dry starch may be added to an alkaline solution of the aminophosphonic acid salt.

The starch reaction is carried out under alkaline conditions, at a pH of 11–13, preferably 11.4–12.4. Alkali may be added to the starch slurry or dispersion either prior to or after the addition of the zwitterion acid reagent. The pH is conveniently controlled by the addition of sodium hydroxide, potassium hydroxide, calcium hydroxide, ammonium hydroxide, tetramethylammonium hydroxide, and the like. The preferred bases are sodium hydroxide and calcium hydroxide.

The reaction is carried out at a temperature of from 20°–100° C., preferably 25°–45° C. It will be recognized by the practitioner that the use of temperatures above about 60° C. with granular starches in an aqueous medium will result in granule swelling and filtration difficulties or in gelatinization of the starch.

When conducting the reaction with granular starches, it may sometimes be desirable to carry out the reaction in the presence of salts, e.g. sodium sulfate, in amount of from about 10 to 40% by weight, based on dry starch. The presence of sodium sulfate acts to suppress swelling of the starch and gives a more filterable product. The sodium sulfate is not used in the calcium hydroxide reactions.

The reaction mixture is agitated under the desired reaction conditions. The reaction time may vary from 0.5 to 20 hours, depending on such factors as the amount, stability and reactivity of the zwitterion reagent employed, the temperature, the pH, the scale of the reaction, and the degree of substitution desired. In general, the preferred range of reaction times is from 1 to 6 hours.

After completion of the reaction, the pH of the reaction mixture is adjusted to a value of from 3 to 7 with any commercial acid such as hydrochloric acid, sulfuric acid, acetic acid, and the like. Such acids may be conveniently added as a dilute aqueous solution.

Recovery of the resulting starch ethers may be readily accomplished, with the particular method employed being dependent on the form of the starch base. Thus, a granular starch is recovered by filtration, optionally washed with water to remove any residual salts, and dried. The granular starch products may also be drum-dried, spray-dried, or gelatinized and isolated by alcohol precipitation or freeze drying to form non-granular products (i.e. gelatinized). If the starch product is non-granular, it may be purified by dialysis to remove residual salts and isolated by alcohol precipitation, freeze drying, or spray drying.

In another method of this invention, the reaction is carried out in an aqueous-organic reaction medium having a water content of from 10 to 80% by weight, depending upon the water-miscible organic solvent selected and the degree of substitution desired in the starch derivative. If too much water is present, the starch may swell or enter into solution thereby complicating recovery and purification. In general, the higher the degree of substitution, the smaller the amount of water which should be used in the reaction medium. The preferred water-miscible solvents are alcohols such as methanol, ethanol, and isopropanol.

The reaction is carried out at a temperature of from 25°–100° C. for a time varying from 0.5 to 12 hours, depending on such factors as the amount, stability and reactivity of the zwitterion reagent, the scale of the reaction, and the degree of substitution desired.

Excess alkali, preferably added as a 20–50% aqueous sodium hydroxide solution, is added to neutralize the zwitterion reagent and catalyze the starch reaction. After completion of the reaction, the alkali is neutralized with any common acid, and the resulting starch ether derivative is recovered by filtration, washed with the aqueous-organic or organic medium, and dried.

If desired, the reaction may be carried out in a substantially dry reaction medium. In one variation of this method, an aqueous solution of zwitterion reagent is added to an agitated starch powder and then an aqueous solution of alkali is added. The preferred alkali is sodium hydroxide which is added as a 20–40% solution. The amount of alkali added should be sufficient to completely neutralize the reagent and then be present in about 1% excess, based on the starch.

The starch mixture is then heated at about 40°–100° C. for about 1–8 hours. The heating time will vary depending on the reaction temperature, starch base used, reagent used, and scale of the reaction. Generally, lower temperatures will require longer reaction times.

After completion of the reaction, the starch mixture is allowed to cool. If removal of any residual salts or by-products is desired, the starch mixture may be suspended in water, the pH adjusted to about 3–7 using any common acid, and the starch derivative recovered by filtration, washing, and isolation.

In addition to preparing the zwitterion starch ether derivatives, it is also within the scope of this invention to prepare modified zwitterion starch ether derivatives which contain, in addition to the novel zwitterion substituent groups described herein, cationic or cationogenic groups comprising primary, secondary, tertiary and quaternary amines and sulfonium and phosphonium groups attached to the starch through ether or ester linkages. For the purposes of this invention, tertiary amino and quaternary ammonium ether groups are preferred. The general method for preparing starches containing tertiary amino groups, which method typically involves reacting starch under alkaline conditions with a dialkylaminoalkyl halide, is described in U.S. Pat. No. 2,813,093. Another method therefor is described in U.S. Pat. No. 3,674,725. The primary and secondary amine starches may be prepared by reacting starch with aminoalkyl anhydrides, aminoalkyl epoxides or halides, or the corresponding compounds containing aryl in addition to alkyl groups.

It is known that quaternary ammonium groups may be introduced into the starch molecule by suitable treatment of the tertiary aminoalkyl ether of starch, as described in U.S. Pat. No. 2,813,093. Alternatively, quaternary groups may be introduced directly into the starch molecule by treatment with the reaction product of an epihalohydrin and a tertiary amino or tertiary amino salt. In either case, the resulting starch is cationic in character and is suitable for use in the novel method of this invention for preparing modified zwitterion starch ether derivatives.

The general preparation of sulfonium derivatives is described in U.S. Pat. No. 2,989,520 and involves essentially the reaction of starch in an aqueous alkaline medium with a beta-halogenoalkylsulfonium salt, vinylsulfonium salt or epoxyalkylsulfonium salt. The general preparation of phosphonium starch derivatives is described in U.S. Pat. No. 3,077,469 and involves essentially reaction of starch in an aqueous alkaline medium with a beta-halogenoalkylphosphonium salt.

Other suitable cationic or cationogenic starches and reagents which provide cationic or cationogenic groups in starches will be apparent to the practitioner, since the zwitterion starch ether derivatives of the present invention comprise any starch treated with a zwitterion reagent which starch is amphoteric in character and which starch has been rendered more cationic in character by the introduction into the starch molecule of an electrically positively charged moiety or a group which is capable of providing an electrically positively charged moiety.

There are three possible ways to prepare the modified zwitterion starch ether derivatives of this invention: (1) a cationic or cationogenic starch derivative is reacted with a zwitterion reagent of this invention, (2) a zwitterion starch ether derivative of this invention is reacted with a cationic or cationogenic reagent(s), or (3) a starch base is reacted in one step with both a zwitterion reagent of this invention and cationic or cationogenic reagent(s).

Where a cationic or cationogenic starch derivative of zwitterion starch ether derivative is reacted with the zwitterion reagent or cationic or cationogenic reagent(s), respectively, to form the modified zwitterion starch ether derivatives in a two-step procedure, the methods for preparing simple cationic or cationogenic starch derivatives and for preparing zwitterion starch ether derivatives are followed, as described in the literature and herein. It is usually not necessary to wash and purify the starch after the first reaction. The skilled practitioner will recognize that starch esters are not very stable at high pH and, hence, modified zwitterion starch ether derivatives containing cationic esters must be prepared by method (2) to avoid ester hydrolysis under the alkaline conditions required to prepare the zwitterion starch ether derivatives of this invention.

In the one-step method for preparing modified zwitterion starch ether derivatives, one variation involves slurrying the starch in water and then adding the zwitterion reagent thereto, bringing the pH to above 11 with a base, adding excess base and the desired amount of the cationogenic or cationic reagent or sequence of reagents, if more than one reagent is employed. The resulting starch mixture is agitated at 20° to 55° C. for 2–16 hours. The reaction time and temperature will depend on the reagent(s) used and the amount of reagent(s) used. After the reaction is complete, the pH is adjusted to about 3–7 using dilute acid and the product is recovered using the same procedure as that used in recovering the zwitterion starch ether derivatives of this invention.

In addition to preparing the zwitterion starch ether derivatives and modified zwitterion starch ether derivatives containing cationogenic or cationic substituent groups, it is also within the scope of this invention to prepare modified zwitterion starch ether derivatives which contain, in addition to the novel zwitterion substituent groups described herein, anionic substituent groups (e.g. carboxyalkyl groups, sulfoalkyl groups, sulfocarboxyalkyl groups, and phosphate groups attached to the starch through ether or ester linkages).

Among the typical reagents used to prepare carboxyalkyl starch ether derivatives are included sodium chloroacetate and salts of 1-halocarboxylic acids such as sodium 1-chloropropionate (see U.S. Pat. No. 2,523,709), sodium 1-bromopropionate and sodium 1-bromoisovalerate (see German Pat. No. 717,275).

Typical reagents used to prepare sulfoalkyl starch ether derivatives are sodium haloalkyl sulfonates such as sodium 2-haloethyl sulfonates (see U.S. Pat. Nos. 2,883,375 and 2,802,000) and sodium 3-chloro-2-hydroxypropyl sulfonate (see U.S. Pat. Nos. 2,825,727 and 2,806,857).

The technique for phosphorylating a starch base is known to those skilled in the art. Thus, U.S. Pat. Nos. 2,824,870, 2,884,412, 2,961,440 and 3,459,632 disclose various phosphorylation techniques consisting essentially of heat reacting starch impregnated with a phosphate salt of an alkali metal, within a prescribed pH range.

Other suitable anionic starches and anionic reagents which provide anionic groups in starches will be apparent to the practitioner, since the zwitterion starch ether derivatives of the present invention comprise any starch treated with a zwitterion reagent which starch is amphoteric in character and which starch has been rendered more anionic in character by the introduction of an electrically negatively-charged moiety into the starch molecule.

There are three possible ways to prepare these modified zwitterion starch ether derivatives: (1) an anionic starch derivative is reacted with a zwitterion reagent of this invention, (2) a zwitterion starch ether derivative of this invention is reacted with an anionic reagent(s), or (3) a starch base is reacted in one step with both a zwitterion reagent of this invention and anionic reagent(s).

The methods for preparing the modified zwitterion starch ether derivatives containing anionic substituent groups are analagous to those described for preparing the modified zwitterion starch ether derivatives containing cationic substituent groups, which are discussed in detail hereinabove.

It can be appreciated by the practitioner that a large number of variations may be effected in reacting the starch base with the zwitterion reagents, the zwitterion and cationic or cationogenic reagents, and the zwitterion and anionic reagents in accordance with the reaction procedures described above without materially departing from the scope and spirit of the invention. Such variations will be evident to those skilled in the art and are to be included within the scope of this invention.

The novel starch ether derivatives of this invention may be used as wet end additives and in many other applications wherein such derivatives are commonly used such as in coatings, sizes, oven cleaners, textile printing, and the like. The starch ether derivatives herein are particularly useful as pigment retention aids in the manufacture of paper. The practitioner will recognize that the structure of the zwitterion starch ether group will vary depending upon the pH of the solution and upon the cations present in the paper pulp. Therefore the exact structure of the modified starch in the paper pulp may be uncertain, and it may contain the same or different cations and one or more cations depending upon the valence of the cations present.

The starch derivatives described herein are used in their dispersed (i.e. cooked) form mainly as beater additives, although their addition to the pulp may occur at any point in the paper-making process prior to the ultimate conversion of the wet pulp into a dry web or sheet. Thus, for example, they may be added to the pulp while the latter is in the headbox, beater, hydropulper or stock chest.

The pigment retention aids of this invention may be effectively used for addition to pulp prepared from any types of cellulosic fibers, synthetic fibers, or combinations thereof. Among the cellulosic materials which may be used are bleached and unbleached sulfate (kraft), bleached and unbleached sulfite, bleached and unbleached soda, neutral sulfite, semi-chemical chemiground wood, ground wood or any combination of these fibers. Fibers of the viscous rayon or regenerated cellulose type may also be used if desired.

Any desired inert mineral fillers may be added to the pulp which is to be modified with the starch ether derivatives herein. Such materials include clay, titanium dioxide, talc, calcium carbonate, calcium sulfate and diatomaceous earths. Rosin or synthetic internal size may also be present, if desired.

The proportion of the starch derivative to be incorporated into the paper pulp may vary in accordance with the particular pulp involved. In general, it is preferred to use about 0.05 to 2% of the starch ether derivative, based on the dry weight of the pulp. Within this preferred range the precise amount which is used will depend upon the type of pulp being used, the specific operating conditions, and the particular end use for which the paper is intended. The use of amounts of starch derivative greater than 2%, based on the dry weight of the pulp, is not precluded, but is ordinarily unnecessary in order to achieve the desired improvements. when added in the proper concentrations, the starch ether derivatives herein serve to increase pigment retention while maintaining the resistance of the finished sheet to folding, picking and scuffing.

The following examples will more fully illustrate the embodiments of this invention. In the examples, all parts and percentages are given by weight, all temperatures are in degrees Celius unless otherwise noted, and D.B. indicates dry basis. The nitrogen content of any particular starch derivative may be determined by comparing the amount of nitrogen contained in the derivative with that of the non-reacted starch base, as determined by the Kjeldahl method. In the Tables all % are determined on a dry basis, based on dry starch.

EXAMPLE I

This example illustrates the preparation of zwitterion reagents for use in the preparation of the novel zwitterion and modified zwitterion starch ether derivatives of this invention. The final solutions were used for the starch reactions described herein, unless otherwise stated.

A. Preparation of N-(2-Chloroethyl)iminobis(methylene)diphosphonic Acid (Zwitterion Reagent A)

A total of 29 parts 2-chloroethylamine hydrochloride was added to 41.5 parts phosphorous acid in 50 parts water. Then 59 parts of 37% aqueous hydrochloric acid were added slowly over the period of about 0.5 hour, and the mixture was slowly brought to reflux over the period of about 1 hour. While maintaining reflux at a constant rate, 81 parts of 37% aqueous formaldehyde were added dropwise over a period of about 0.75 hours. The mixture was refluxed for 3 hours, cooled to 24° C. and stripped of volatiles at 40° C. in a rotary evaporator (water aspirator) to yield a concentrate. An equal amount of water (i.e. 84 parts) was added to the concentrate and the pH was raised to 1.5 with 25% aqueous sodium hydroxide while maintaining the temperature at below 35° C.

B. Preparation of N-(2-Bromoethyl)iminobis(methylene)diphosphonic Acid (Zwitterion Reagent B)

The procedure described in Preparation A was followed except that 51 parts 2-bromoethylamine hydrobromide, 100 parts of 48% aqueous hydrobromic acid and 81 parts of 37% aqueous formaldehyde were used. Then 109 parts water were added to the concentrate and the pH was raised to 2.5.

C. Preparation of N-(Ethyl)-N-(2-chloroethyl)aminomethylphosphonic Acid (Zwitterion Reagents C-1 and C-2)

The procedure described in Preparation A was followed except that 36 parts and 72 parts of N-(2-chloroethyl)ethylamine hydrochloride were used to prepare Reagents C-1 and C-2, respectively. Then 75 parts water were added and the pH adjusted to 1.5.

D. Preparation of N-(n-Butyl)-N-(2-chloroethyl)aminomethylphosphonic Acid (Zwitterion Reagents D-1 and D-2)

The procedure described in Preparation C was followed except that 43 parts and 86 parts of N-(2-chloroethyl)-n-butylamine hydrochloride were used instead of N-(2-chloroethyl)ethylamine hydrochloride to prepare Reagents D-1 and D-2, respectively.

E. Preparation of N-(Cyclohexyl)-N-(2-chloroethyl)-aminomethylphosphonic Acid (Zwitterion Reagents E-1 and E-2)

The procedure described in Preparation C was followed except that 40 parts of N-(2-chloroethyl)cyclohexylamine hydrochloride were used instead of N-(2-chloroethyl)ethylamine hydrochloride to prepare Reagent E-1.

A total of 101 parts of N-(2-chloroethyl)cyclohexylamine hydrochloride, 41.5 parts phosphorous acid in 101 parts water, 75 parts of 37% aqueous hydrochloric acid, and 104 parts of 37% aqueous formaldehyde were used to prepare Reagent E-2.

F. Preparation of N-(2-Chloroethyl)alkylamine Hydrochlorides

These reagents, specifically N-(2-chloroethyl)ethylamine hydrochloride, N-(2-chloroethyl)-n-butylamine hydrochloride, and N-(2-chloroethyl)cyclohexylamine hydrochloride, were used in the preparation of the new Zwitterion Reagents C-1, C-2, D-1, D-2, E-1, and E-2, described hereinabove.

1. A total of 22 parts 2-(ethylamino)ethanol was added to 75 parts toluene and the solution was cooled to −10° C. Then a solution of 33 parts thionyl chloride in 25 parts toluene was slowly added with agitation over 2.5 hours while maintaining the temperature at below −10° C. The mixture was brought to a temperature of about 100° C. and 100 parts toluene were added. The mixture was agitated for 1 hour, cooled to 82° C., and maintained at 82° C. for 3 hours and then cooled to 24° C. N-(2-Chloroethyl)ethylamine hydrochloride was recovered by filtration and washed with toluene.

2. The procedure described in Preparation F-1 was followed except that 29 parts 2-(n-butylamino)ethanol were used instead of 2-(ethylamino)ethanol and the mixture was heated at 75° C. for 2.5 hours instead of 1 hour at 100° C. followed by 3 hours at 82° C. N-(2-Chloroethyl)n-butylamine hydrochloride was recovered.

3. The procedure described in F-1 was followed except that 35.8 parts of N-(2-hydroxyethyl)cyclohexylamine were used instead of 2-(ethylamino)ethanol, the toluene was increased to 175 parts, and the mixture was heated for 3 hours at 70° C. N-(2-Chloroethyl)cyclohexylamine hydrochloride was recovered.

EXAMPLE II

This example illustrates the preparation of various zwitterion starch ether derivatives using corn starch as the base.

A. Preparations Using N-(2-Chloroethyl)iminobis(methylene)diphosphonic Acid (Zwitterion Reagent A)

1. A total of 2 parts of a 36.0% aqueous solution of Zwitterion Reagent A (0.72 parts D.B.) was added to a slurry of 50 parts corn starch in 65 parts water. The pH was raised to 11.4 with calcium hydroxide (0.94 parts) and then 0.5 part calcium hydroxide (1% excess on starch) was added (pH was 11.8). The mixture was agitated for 6 hours at 40° C. The pH was lowered from 11.4 to 3.0 by the addition of 9.5% aqueous hydrochloric acid. The starch derivative was recovered by filtration, washed three times with acidic water (pH 3) and air dried. It contained 0.12% N (D.B.).

2. A total of 50 parts of corn starch and 6.44 parts of a 31.2% aqueous solution of Zwitterion Reagent A (2.01 parts D.B.) was added to a solution of 3 parts of 50% aqueous sodium hydroxide (1.5 parts D.B.) and 12.5 parts sodium sulfate in 65 parts water. The mixture was agitated for 6 hours at 32° C., the pH was lowered from 11.8 to 3.0, and the starch derivative recovered as described above. It contained 0.11% N (D.B.).

B. Preparation Using N-(2-Bromoethyl)iminobis(methylene)diphosphonic Acid (Zwitterion Reagent B)

The procedure described in Preparation A-1 was followed except that 25.5 parts of a 23.5% aqueous solution of Zwitterion Reagent B (6.0 parts D.B.) were used, 4.26 parts calcium hydroxide were needed to raise the pH to 11.5, and reaction temperature and pH were 35° C. and 12.1. The starch derivative contained 0.12% N (D.B.).

C. Preparations Using N-(Ethyl)-N-(2-chloroethyl)aminomethylphosphonic Acid (Zwitterion Reagents C-1 and C-2)

The procedure described in Preparation A-1 was followed except that 12.4 parts of a 24.3% aqueous solution of Zwitterion Reagent C-1 (3.0 parts D.B.) were used, 3.3 parts parts calcium hydroxide were needed to raise the pH to 11.5, and reaction temperature and pH were 34° C. and 11.9. The starch derivative contained 0.27% N (D.B.).

The same procedure was followed except that 9.3 parts of a 43.0% aqueous solution of Zwitterion Reagent C-2 (4.0 parts D.B.) were used and 4.1 parts of calcium hydroxide were needed to raise the pH to 11.6. The 0.5 parts excess of calcium hydroxide was omitted. The starch derivative contained 0.35% N (D.B.).

D. Preparations Using N-(n-Butyl)-N-(2-chloroethyl)aminomethylphosphonic Acid (Zwitterion Reagents D-1 and D-2)

The procedure described in Preparation A-1 was followed except that 14.8 parts of a 20.2% aqueous solution of Zwitterion Reagent D-1 (3.0 parts D.B.) were used, 4.5 parts calcium hydroxide were required to raise the pH to 11.8, and reaction temperature and pH were 34° C. and 12.1. The starch derivative contained 0.27% N (D.B.).

The same procedure was followed except that 13.8 parts of a 29.3% aqueous solution of Zwitterion Reagent D-2 (4.0 parts D.B.) were used and 4.4 parts of calcium hydroxide were needed to raise the pH to 11.6. The 0.5 part excess of calcium hydroxide was omitted. The starch derivative contained 0.35% N (D.B.).

E. Preparations Using N-(Cyclohexyl)-N-(2-chloroethyl)aminomethylphosphonic Acid (Zwitterion Reagents E-1 and E-2)

The procedure described in Preparation A-1 was followed except that 11.6 parts of a 20.3% aqueous solution of Zwitterion Reagent E-1 (2.35 parts D.B.) were used, 4.0 parts calcium hydroxide were needed to raise the pH to 11.4, and reaction temperature and pH were 35° C. and 11.9. The starch derivative contained 0.21% N(D.B.).

The same procedure was followed except that 20.1 parts of a 19.9% aqueous solution of Zwitterion Reagent E-2 (4.0 parts D.B.) were used, 4.1 parts of calcium hydroxide were needed to raise the pH to 11.6, and the reaction temperature was 35° C. The 0.5 part excess of calcium hydroxide was omitted. The starch derivative contained 0.25% N (D.B.).

EXAMPLE III

This example illustrates the preparation of modified zwitterion starch ether derivatives containing cationic or cationogenic groups.

A. Preparation of Derivatives Containing Amino-Diphosphonic Acid Salt Groups and Diethyl Aminoethyl Ether Groups 1. Simultaneous Reaction. A total of 2.2 parts of a 34.4% aqueous solution of N-(2-chloroethyl)iminobis(methylene)diphosphonic acid (Zwitterion Reagent A) (0.75 parts D.B.) was added to a slurry of 50 parts corn starch in 65 parts water. The pH was raised to 12.1 with calcium hydroxide (1.1 parts). Then 0.75 parts calcium hydroxide (1.5% excess) and 3 parts of a 50% aqueous solution of 2-diethylaminoethylchloride hydrochloride (Cationic Reagent A) (1.5 parts D.B.) were added. The mixture was agitated for 6 hours at 40° C. The pH was lowered from 11.8 to 3.0 with aqueous 9.5% hydrochloric acid. The starch derivative was recovered by filtration, washed three times with water and air dried. It contained 0.30% N (D.B.).

Using this procedure a series of starch derivatives were prepared with variations in temperature and treatment levels of the two reagents. The data is summarized in Table I.

TABLE I

| Zwitterion Reagent A % | Cationic Reagent A % | Temperature °C. | %N (D.B.) |
|---|---|---|---|
| 0.37 | 3.0 | 40 | 0.28 |
| 0.75 | 3.0 | 40 | 0.26 |
| 1.50 | 3.0 | 40 | 0.30 |
| 2.25 | 3.0 | 40 | 0.31 |
| 1.50 | 1.0 | 40 | 0.16 |
| 1.50 | 2.0 | 40 | 0.24 |
| 1.50 | 3.0 | 40 | 0.31 |
| 1.50 | 4.0 | 40 | 0.37 |
| 4.45 | 1.0 | 24 | 0.23 |
| 4.45 | 2.0 | 24 | 0.26 |
| 4.45 | 3.0 | 24 | 0.30 |
| 4.45 | 4.0 | 24 | 0.31 |

2. Consecutive Reaction. A total of 4 parts of a 50% aqueous solution of Cationic Reagent A (2.0 parts D.B.) and 1.5 parts calcium hydroxide was added to a slurry of 50 parts corn starch in 65 parts water. The mixture was agitated at 40° C. for 6 hours and the pH was then lowered to 3.0 with 9.5% aqueous hydrochloric acid. The cationic starch ether derivative was recovered by filtration, washed with water and air dried. It contained 0.34% N (D.B.). It was reslurried in 65 parts water and 4.4 parts of a 30.4% aqueous solution of Zwitterion Reagent A (1.3 parts D.B.) were added. The pH was raised to 11.9 with calcium hydroxide (1.7 parts). The mixture was agitated for 6 hours at 23°–25° C., the pH was lowered to 3.0 with 9.5% aqueous hydrochloric acid, and the resulting modified starch derivative was recovered by filtration, washed with water, and air dried. It contained 0.41% N (D.B.).

B. Preparation of Derivative Containing Amino-Diphosphonic Acid Salt Groups and 3-(Trimethylammonium chloride)-2-hydroxypropyl Ether Groups Consecutive Reaction. A total of 24.0 parts of 12.5% aqueous potassium hydroxide (3.0 parts D.B.) was added to a slurry of 100 parts corn starch in 125 parts water. Then 6.2 parts of a 50% aqueous solution of the reaction product of epichlorohydrin and trimethylamine, i.e. 3-chloro-2-hydroxypropyltrimethylammonium chloride (3.1 parts D.B.), were added. The mixture was agitated at 40° C. for 6 hours and the pH was then lowered to 4.5 with 10% aqueous hydrochloric acid. The cationic starch ether derivative was recovered by filtration, washed with water and air dried. It contained 0.22% N (D.B.). A total of 50 parts of this derivative was reslurried in 65 parts water. Then 7.8 parts of a 38.3% aqueous solution of Zwitterion Reagent A (3.0 parts D.B.) and 2.7 parts calcium hydroxide were added. The mixture was agitated for 6 hours at 33° C. The pH was then lowered from 11.8 to 3.0 with 9.5% aqueous hydrochloric acid. The resulting modified starch derivative was recovered by filtration, washed with water, and air dried. It contained 0.30% N (D.B.)

EXAMPLE IV

This example illustrates the preparation of modified zwitterion starch ether derivatives containing anionic groups.

A. Preparation of Derivatives Containing Amino-Diphosphonic Acid Salt Groups and 2-Sulfo-2-carboxyethyl Ether Groups 1. Simultaneous Reaction. A total of 1.0 parts of 3-chloro-2-sulfopropionic acid (Anionic Reagent A) and 6.8 parts of 27.75% aqueous solution of Zwitterion Reagent A (1.9 parts D.B.) was added to a slurry of 50 parts of corn starch in 65 parts water. The pH was raised to 11.0 with calcium hydroxide (2.1 parts). Then 1.0 part calcium hydroxide (2% excess) was added. The mixture was agitated for 6 hours at 24° C. The pH was lowered from 12.0 to 3.0 with aqueous 9.5% hydrochloric acid. The starch derivative was recovered by filtration, washed three times with water and air dried. It contained 0.16% N (D.B.).

2. Consecutive Reaction. A total of 6.8 parts of a 27.75% aqueous solution of Zwitterion Reagent A (1.9 parts D.B.) was added to a slurry of 50 parts corn starch in 65 parts water. The pH was raised to 11.8 with calcium hydroxide (2.1 parts). Then 0.5 part calcium hydroxide (1% excess) was added. The mixture was agitated for 5 hours at 24° C. The post reaction pH was 12.2. Then a total of 1.0 part of Anionic Reagent A was added together with sufficient calcium hydroxide, if necessary, to keep the pH above 11.0. An additional 0.25 part calcium hydroxide (0.5% excess) was then added and the mixture was agitated for 1 hour at 24° C. The pH was lowered from 11.6 to 3.0 with 9.5% aqueous hydrochloric acid. The starch derivative was recovered as described above. It contained 0.13% N (D.B.).

Using these simultaneous and consecutive reaction procedures a series of starch derivatives were prepared with variations in the treatment levels of Anionic Reagent A. The data is summarized in Table II.

EXAMPLE V

This example illustrates the preparation of additional zwitterion starch ether derivatives using different granular starch bases and N-(2-chloroethyl)iminobis(methylene)diphosphonic acid (Zwitterion Reagent A). The reactions were carried out according to the procedure described in Example II, Preparation A-1, except that the reaction was done at 24° C. rather than 40° C. The data is summarized in Table III.

TABLE II

| Zwitterion Reagent A % | Anionic Reagent A % | % N (D.B.) |
|---|---|---|
| Simultaneous | | |
| 4.0 | 1.0 | 0.16 |
| 4.0 | 2.0 | 0.16 |
| 4.0 | 3.0 | 0.15 |
| 4.0 | 4.0 | 0.15 |
| Consecutive | | |
| 4.0 | 1.0 | 0.11 |
| 4.0 | 2.0 | 0.13 |
| 4.0 | 3.0 | 0.12 |
| 4.0 | 4.0 | 0.12 |

TABLE III

| Base Starch | Zwitterion Reagent A % | % N (D.B.) |
|---|---|---|
| Tapioca | 4.8 | 0.09 |
| Waxy Maize previously treated with 7.0% propylene oxide and 0.02% epichlorohydrin | 4.8 | 0.11 |
| High Amylose Corn Starch (50% wt. % amylose) | 4.8 | 0.21 |
| Corn Starch (oxidized by reaction with NaOCl to 75 fluidity) | 4.8 | 0.12 |

EXAMPLE VI

This example illustrates the preparation of zwitterion starch ether derivatives using a non-granular corn starch base and N-(2-chloroethyl)iminobis(methylene)-diphosphonic acid (Zwitterion Reagent A).

A slurry of 75 parts waxy maize starch (which had been acid-converted to a degree known in the trade as 85 fluidity) in 300 parts water was cooked in a boiling water bath for 20 minutes, while agitating the mixture for the first 3 minutes. After cooling (to 24° C.), the pH was raised to 12.2 with 25% aqueous sodium hydroxide. A total of 43 parts of a 25.3% aqueous Zwitterion Reagent A (10.9 parts D.B.) was added over a period of 45 minutes while maintaining a pH of 12.2 with 25% aqueous sodium hydroxide. The mixture was agitated for 2 hours while maintaining the pH at 12.2 by adding 25% aqueous sodium hydroxide when required. The pH was lowered to 3.0 with 9.5% aqueous hydrochloric acid and the mixture was dialyzed in distilled water for 27 hours. The starch derivative was recovered by freeze drying the dialyzed solution. It contained 0.43% N (D.B.).

Using this procedure a series of starch derivatives were prepared with variations in the temperature, time, % reagent and alkali. The data is summarized in Table IV.

TABLE IV

| Reaction Conditions | | Zwitterion | | |
|---|---|---|---|---|
| Temperature (°C.) | Time (hours) | Reagent A % | Alkali | % N (D.B.) |
| 24° | 2.0 | 14.5 | NaOH | 0.43 |
| 24° | 2.0 | 60.9 | NaOH | 1.22 |
| 80° | 0.75 | 14.5 | NaOH | 0.36 |
| 43° | 2.0 | 17.8 | KOH | 0.48 |

EXAMPLE VII

This example illustrates the preparation of various zwitterion and modified zwitterion starch ether derivatives of this invention and their use as pigment retention aids in the manufacture of paper. The derivatives prepared include Starch A (a zwitterion starch ether derivative), Starch B (a modified zwitterion starch ether derivative containing anionic groups), Starches C, E, F & G (modified zwitterion starch ether derivatives containing cationic groups), and Starch D (comparative—a cationic starch ether derivative containing no zwitterion groups).

Part I

Starch A: A total of 4.5 parts of crystalline N-(2-chloroethyl)iminobis(methylene)diphosphonic acid (Zwitterion Reagent A) was added to a slurry of 100 parts corn starch in 125 parts water. The pH was raised to 11.9 with calcium hydroxide (5.2 parts). The mixture was agitated for 6.25 hours at 40° C. The pH was lowered to 3.0 by the addition of 9.5% aqueous hydrochloric acid. The starch derivative was recovered by filtration, washed with acidic water (pH 3) and air dried. It contained 0.21% N (D.B.).

Starch B: A total of 6.77 parts of 37.0% aqueous solution of Zwitterion Reagent A (2.5 D.B.) was added to a slurry of 50 parts corn starch in 65 parts water. The pH was raised to 12.0 with calcium hydroxide (2.6 parts). The mixture was agitated for 5 hours at 23° C. Then a total of 1.0 part of 3-chloro-2-sulfopropionic acid (Anionic Reagent A) and 0.25 parts calcium hydroxide were added. The mixture was agitated for 1 hour at 23° C. The pH was lowered to 3.0 with 9.5% aqueous hydrochloric acid. The starch derivative was recovered as described above. It contained 0.13% N (D.B.).

Starch C: A total of 2 parts 2-diethylaminoethylchloride hydrochloride (Cationic Reagent A) and 1.5 parts calcium hydroxide was added to a slurry of 50 parts corn starch in 65 parts water. The mixture was agitated for 6 hours at 40° C. The pH was then lowered to 3.0 with 9.5% aqueous hydrochloric acid. The cationic starch ether derivative (Starch D) was recovered as described above; it contained 0.34% N (D.B.). Starch D was then reslurried in 65 parts water and 4.39 parts of a 30.4% aqueous solution of Zwitterion Reagent A (1.33 parts D.B.) were added. The pH was raised to 11.9 with calcium hydroxide (1.76 parts). The mixture was agitated for 6 hours at 23° C. The pH was lowered to 3.0 with 9.5% aqueous hydrochloric acid. The starch derivative (Starch C) was recovered as described above; it contained 0.41% N (D.B.).

Starch D: See the first half of the preparation of Starch C for details.

Starch E: It was prepared in the same manner as Starch C except that 1.03 parts of a 24.27% aqueous solution of N-(ethyl)-N-(2-chloroethyl)aminomethylphosphonic acid (Zwitterion Reagent C) (0.25 part D.B.) and 1.3 parts calcium hydroxide were used. The starch derivative contained 0.33% N (D.B.).

Starch F: It was prepared in the same manner as Starch E except that 4.12 parts of Zwitterion Reagent C solution (1.0 part D.B.) and 1.9 parts calcium hydroxide were used. It contained 0.41% N (D.B.).

Starch G: It was prepared in the same manner as Starch C except that 0.97 parts Zwitterion Reagent A solution (0.25 part D.B.) and 1.25 parts calcium hydroxide were used. It contained 0.34% N (D.B.).

Part II

Each starch product prepared above was divided into three portions, and each portion was dispersed by cooking in water at atmospheric pressure in a conventional manner. Then the cooked portions were added at a concentration of 0.25%, based on the weight of the dry pulp, to a bleached sulfite pulp which contained a varied amount of paper alum, i.e. aluminum sulfate. The three pulps contained 0%, 4.0% and 11.0% alum, by weight based on the dry pulp. In each case, the pigment retention value of the test paper stock and those of a control were determined by first preparing paper sheets on the Williams Standard Sheet Mold and then testing for the percent of titanium dioxide ($TiO_2$) retained by the method described in TAPPI Standard #T413 m. 58. The control consisted of an amphoteric starch ether derivative of the prior are, i.e. the phosphorylated, diethylaminoethyl ether of corn starch, containing 0.32% nitrogen and 0.08% phosphorus by weight, prepared as described in U.S. Pat. No. 3,459,632.

The results of the pigment retention determinations are summarized in Tables V to VIII below.

TABLE V

| | % $TiO_2$ Retention in the presence of the following amounts of alum* | | |
|---|---|---|---|
| Material Tested | 0% | 4.0% | 11.0% |
| Blank | 30.0 | 35.0 | 28.0 |
| Control (amphoteric starch ether) | 56.5 | 64.0 | 44.0 |
| Starch A (zwitterion starch ether) | 53.0 | 62.5 | 40.0 |

*Based on the percent by weight of the dry pulp, yielding pH values of 8.1, 6.3, and 4.5%, respectively.

The data in Table V indicate that the zwitterion starch ether derivative containing amino-diphosphonic acid groups (or salt groups) had anionic as well as cationic properties. It provided a pigment retention comparable to that of the amphoteric starch ether derivative used as the control.

TABLE VI

| | % $TiO_2$ Retention in the presence of the following amounts of alum* | | |
|---|---|---|---|
| Material Tested | 0% | 4.0% | 11.0% |
| Blank | 38.5 | 43.2 | 30.1 |

TABLE VI-continued

| Material Tested | % TiO$_2$ Retention in the presence of the following amounts of alum* | | |
|---|---|---|---|
| | 0% | 4.0% | 11.0% |
| Control (amphoteric starch ether) | 55.2 | 70.2 | 42.8 |
| Starch B (zwitterion starch ether containing anionic groups) | 50.3 | 68.1 | 53.2 |

*Based on the percent by weight of the dry pulp, yielding pH values of 7.8, 6.1 and 4.5%, respectively.

The data in Table VI indicate that the modified zwitterion starch ether derivative containing amino-diphosphonic acid groups (or salt groups) and 2-sulfo-2-carboxyethyl ether groups as anionic groups retained its cationic properties in neutral systems (0% alum) and provided greatly improved pigment retention in high alum-containing systems (11% alum).

TABLE VII

| Material Tested | % TiO$_2$ Retention in the presence of the following amounts of alum* | | |
|---|---|---|---|
| | 0% | 4.0% | 11.0% |
| Blank | 30.4 | 38.5 | 30.6 |
| Control (amphoteric starch ether) | 55.7 | 69.9 | 45.6 |
| Starch D (cationic starch ether) (Comparative) | 61.0 | 45.3 | 32.0 |
| Starch C (zwitterion starch ether containing cationic groups) | 67.6 | 72.1 | 42.1 |

*Based on the percent by weight of the dry pulp.

The data in Table VII indicate that the control amphoteric starch ether provided improved pigment retention in alum-containing systems, but slightly poorer retention in neutral systems when compared with Starch D, the comparative cationic starch ether containing diethyl aminoethyl ether groups. Starch D provided good pigment retention in neutral systems (0% alum), but relatively poor pigment retention in alum-containing systems. Starch C, a modified zwitterion starch ether derivative containing amino-diphosphonic acid groups (or their salts) and diethyl aminoethyl ether groups as cationic groups, provided unique pigment retention properties. It gave very good retention in alum-containing systems (equivalent to the amophoteric starch ether control); however instead of a decrease in pigment retention in neutral systems (in comparison with cationic Starch D) it gave an increase in pigment retention. Thus, Starch C has the pigment retention properties of a cationic starch ether in neutral systems as well as the properties of an amphoteric starch ether in acidic (alum-containing) systems.

TABLE VIII

| Material Tested | % TiO$_2$ Retention in the presence of the following amounts of alum* | | |
|---|---|---|---|
| | 0% | 4.0% | 11.0% |
| Blank | 21.0 | 58.2 | 55.3 |
| Control (amphoteric starch ether) | 64.0 | 84.4 | 74.6 |
| Starch D (cationic starch ether) (Comparative) | 73.5 | 68.6 | 60.2 |
| Starch E (zwitterion starch ethers | 74.5 | 86.6 | 75.0 |
| Starch F containing cationic groups) | 73.9 | 89.4 | 82.4 |
| Starch G | 74.4 | 86.1 | 73.6 |

*Based on the percent by weight of the dry pulp, yielding pH values of 8.2, 6.2, and 4.6, respectively.

The data in Table VIII indicate that small amounts of amino-diphosphonic acid substitutents (Starch G) and amino-monophosphonic acid substituents (Starches E and F) in zwitterion starch ethers containing diethyl aminoethyl ether groups as cationic groups provided large improvements in pigment retention in alum systems, while maintaining good pigment retention in neutral systems (0% alum), when compared to Starch D, a cationic starch ether derivative containing only diethyl aminoethyl ether groups.

EXAMPLE VIII

This example illustrates the preparation of a zwitterion starch ether derivative using an aqueous-organic medium.

A total of 30 parts corn starch was added to 180 parts of 50% aqueous isopropanol. Then 3.6 parts of 50% aqueous sodium hydroxide (1.8 parts D.B.) and 38.1 parts of a 19.7% aqueous solution of N-(2-chloroethyl)iminobis(methylene)diphosphonic acid (Zwitterion Reagent A) (7.5 parts D.B.) were added. An additional 6.9 parts of 50% aqueous sodium hydroxide were added (pH 11.5) and the mixture was agitated for 4 hours at 40° C. The pH was lowered to 8.3 with dilute acetic acid. The starch derivative was recovered by filtration, washed with 50% aqueous isopropanol and then with isopropanol, and air dried. It contained 0.67% N (D.B.).

EXAMPLE IX

This example illustrates the preparation of a zwitterion starch ether derivative using a substantially dry process.

A total of 50 parts corn starch was agitated in a Hobart mixer and 17.4 parts of a 17.4% aqueous solution of N-(2-chloroethyl)iminobis(methylene)diphosphonic acid (Zwitterion Reagent A) (3.0 parts D.B.) were added slowly. Then 10.0 parts of 25% aqueous sodium hydroxide (2.5 parts D.B.) were added dropwise. The mixture was agitated for 15 minutes and then placed in an oven and heated at 75° C. for 3 hours. The starch was suspended in 125 parts water, and the pH was lowered to 5.0 with 10% aqueous hydrochloric acid. The starch derivative was recovered by filtration, washed three times with 300 parts 50% aqueous ethanol, and air dried. It contained 0.13% N (D.B.).

Summarizing, this invention is seen to provide novel zwitterion starch ether derivatives containing amino-diphosphonic acid groups or amino-monophosphonic acid groups (or their salts) and modified zwitterion derivatives containing, in addition to the phosphonic acid groups, cationic or anionic groups. All of these derivatives may be used as pigment retention aids in paper.

Now that the preferred embodiments of the present invention have been described in detail, various modifications and improvements thereon will become readily apparent to those skilled in the art. Accordingly, the spirit and scope of the invention are to be limited only by the appended claims and not by the foregoing specification.

What is claimed is:

1. As a composition of matter, a compound of the general structure

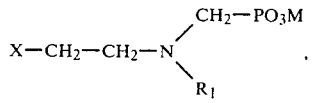

wherein X is a halogen, M is a cation, and $R_1$ is a $C_1$–$C_6$ group or a $C_3$–$C_6$ cycloalkyl group.

2. The compound of claim 1, wherein X is chlorine or bromine, M is hydrogen, an alkali or an alkaline earth metal, and $R_1$ is a ethyl, n-butyl, or cyclohexyl group.

3. The compound of claim 2, wherein X is chlorine and M is hydrogen or sodium.

* * * * *